United States Patent [19]

Tamura et al.

[11] 4,249,019

[45] Feb. 3, 1981

[54] PROCESS FOR PRODUCING CARBOXYLIC ESTERS

[75] Inventors: Nobuhiro Tamura; Yohei Fukuoka; Setsuo Yamamatsu; Yoshio Suzuki; Ryoichi Mitsui, all of Fuji; Tadayuki Ibuki, Fuchu, all of Japan

[73] Assignee: Asahi Kasei Kogyo Kabushiki Kaisha, Osaka, Japan

[21] Appl. No.: 960,324

[22] Filed: Nov. 13, 1978

[30] Foreign Application Priority Data

Nov. 17, 1977 [JP] Japan .................................. 52-137267
Nov. 17, 1977 [JP] Japan .................................. 52-137268
Nov. 17, 1977 [JP] Japan .................................. 52-137271

[51] Int. Cl.³ ............... C07C 67/39; C07C 69/14; C07C 69/54; C07C 69/78
[52] U.S. Cl. .................... 560/208; 260/410; 260/410.5; 260/410.6; 260/410.9 N; 260/410.9 R; 560/1; 560/77; 560/103; 560/105; 560/106; 560/109; 560/112; 560/113; 560/131; 560/190; 560/193; 560/198; 560/201; 560/238
[58] Field of Search ............... 560/1, 238, 208, 106, 560/109, 103, 201, 190, 193, 198, 105, 77, 131, 112, 113; 260/410.5, 410.6, 410.9 R, 410.9 N, 410

[56] References Cited

U.S. PATENT DOCUMENTS

| 2,212,900 | 8/1940 | Groll et al. | 560/208 |
| 3,257,448 | 6/1966 | Clark et al. | 560/238 |
| 3,639,446 | 2/1972 | Kunugi | 560/238 |
| 3,772,381 | 11/1973 | Nakamura et al. | 560/208 |

FOREIGN PATENT DOCUMENTS

| 966809 | 8/1964 | United Kingdom | 560/243 |
| 1121877 | 7/1968 | United Kingdom | 560/238 |

*Primary Examiner*—Vivian Garner
*Attorney, Agent, or Firm*—Sprung, Felfe, Horn, Lynch & Kramer

[57] ABSTRACT

A carboxylic ester is produced in one step in a high yield and with a high selectivity by reacting an aldehyde with an alcohol in the presence of oxygen by using a catalyst comprising (I) palladium, (II) at least one compound selected from the group consisting of lead compounds, thallium compounds and mercury compounds and (III) at least one compound selected from the group consisting of alkali metal compounds and alkaline earth metal compounds.

9 Claims, No Drawings

PROCESS FOR PRODUCING CARBOXYLIC ESTERS

This invention relates to a process for producing in one step a carboxylic ester by the oxidation of an aldehyde and an alcohol with molecular oxygen. More particularly, it relates to a process for producing a carboxylic ester in a high yield by carrying out the reaction in the presence of a specific catalyst.

The process for producing a carboxylic ester by oxidizing an aldehyde and an alcohol with molecular oxygen is important from the industrial point of view. Particularly, it would be of great significance if when an $\alpha,\beta$-unsaturated aliphatic aldehyde, for example, acrolein or methacrolein is used as the aldehyde an $\alpha,\beta$-unsaturated acid ester, for example, acrylic ester or methacrylic ester could be produced in one step. There has heretofore been known a process for producing an $\alpha,\beta$-unsaturated carboxylic ester from an $\alpha,\beta$-unsaturated aldehyde by first oxidizing the aldehyde to a carboxylic acid and then esterifying the carboxylic acid in a separate step. Such a process has disadvantages in that two reaction steps are necessary and a limit exists in improvement in yield because the oxidation of an aldehyde is generally carried out in the gas phase at high temperatures. Moreover, since the esterification is inherently a reversible reaction, large facilities are necessary to recycle a large quantity of unreacted starting materials.

In spite of many efforts which were made over a long period of time to solve the above-said problems, none of them have succeeded in developing the commercial oxidation of methacrolein into methacrylic acid which is further esterified into methyl methacrylate. Therefore, there still exists a strong demand for the development of a technique of producing an $\alpha,\beta$-unsaturated aliphatic carboxylic ester, by which the above-mentioned yield problem and the problems of high cost of facilities and running resulting from two reaction steps can be solved.

In order to solve the problems, it is required not only to oxidize and esterify an aldehyde in a single step but also to produce the intended carboxylic ester in a high yield, that is, with a high conversion and with little by-products, and, in addition, without consuming much time in isolation of the final product. No report has been published on the technique capable of meeting such requirements. This is because the aldehyde used in the reaction is very unstable and tends to produce many by-products beside the intended product. The by-products include, for example, an acetal, dimer, trimer, higher polymers, and carboxylic acids, and when an unsaturated aldehyde is used, an alkoxy compound is formed as by-product by addition of the alcohol to the unsaturated bond of the aldehyde. Further, the combustion products such as carbon dioxide, carbon monoxide and water are, of course, expected. Of these by-products, the carboxylic acid (for example, acrylic acid in the case of acrolein) is not a by-product causing a decrease in product yield but is undesirable, because it is liable to cause trouble in the equipment or operation. It is very difficult, however, to produce substantially quantitatively a carboxylic ester from an aldehyde without forming a significant amount of such by-products.

Aiming at the solution of the problems, the present inventors have made extensive studies on the method for producing in one step and in a high yield a carboxylic ester from an aldehyde and an alcohol by oxidation with molecular oxygen. As a result, it has surprisingly been found that the intended carboxylic ester can be obtained in a high yield even at room temperature and atmospheric pressure, when there is used in the above reaction a catalyst comprising (I) palladium, (II) at least one compound selected from the group consisting of lead compounds, thallium compounds and mercury compounds, and (III) at least one compound selected from the group consisting of alkali metal compounds and alkaline earth metal compounds. Table 1 shows some examples together with a few comparative examples to make the above findings clearer.

Table 1

| Run No. | Catalyst | MAcr Conv. (%) | MMA yield (%) | MMA Selec.*1 (%) | Productivity*2 | Remarks |
|---|---|---|---|---|---|---|
| 1 | Pd(5 wt-%)—SiO$_2$ | 14 | 6 | 43 | 1.5 | U.S.P. 3,639,449 |
| 2 | Pd(5 wt-%)—Mg(OAc)$_2$—SiO$_2$ | 21 | 14 | 67 | 3.5 | Comparison |
| 3 | Pd(5 wt-%)—Pb(OAc)$_2$—SiO$_2$ | 55 | 41 | 75 | 10 | |
| 4 | Pd(5 wt-%)—Pb(OAc)$_2$—Mg(OAc)$_2$—SiO$_2$ | 98 | 88 | 90 | 51 | Present invention |
| 5 | Pd(5 wt-%)—Pb(OAc)$_2$—LiOAc—SiO$_2$ | 99 | 85 | 86 | 33 | |

[1] In the catalyst, the Pb compound was supported in an amount of 5% by weight as metallic Pb, the Mg compound in an amount of 2.5% by weight as metallic Mg, and the Li compound in an amount of 2.5% by weight as metallic Li.
[2] Reaction conditions: Batch system in a 500-cc flask; MAcr/MeOH = 12 cc/300 cc; catalyst, 12 g; O$_2$, 15 liters/hour; temperature, 40° C.; reaction time, 2 hours.
[3] MAcr = methacrolein; MMA = methyl methacrylate; Ac = acetyl.

*1 MMA selec. = $\frac{\text{MMA yield}}{\text{MAcr conv.}} \times 100$ (%)

*2 Productivity = $\frac{\text{MMA (g/hour)}}{\text{Pd charged (g)}}$

Table 1 shows that the above-said surprising fact indicates such a remarkable reaction behavior that by the use of a catalyst of this invention, not only the combustion of starting materials scarcely takes place, but also the formation of a dimer and higher polymers originated from an unsaturated aldehyde is substantially suppressed. It is suggested that the catalyst of this invention is commercially advantageous and greatly different in the mechanism of catalytic action from the conventional one.

According to this invention, there is provided a process for producing a carboxylic ester by the reaction between an aldehyde and an alcohol in the presence of oxygen with a catalyst, characterized in that as said catalyst there is used a mixture comprising (I) palladium, (II) at least one compound selected from the group consisting of lead compounds, thallium compounds and mercury compounds, and (III) at least one compound selected from the group consisting of alkali metal compounds and alkaline earth metal compounds.

The aldehydes used in this invention include saturated aliphatic aldehydes such as formaldehyde, acetaldehyde, propionaldehyde and isobutyraldehyde; unsaturated aliphatic aldehydes such as acrolein, methacrolein and crotonaldehyde; aromatic aldehydes such as benzaldehyde, tolualdehyde, benzylaldehyde and phthalaldehyde; further, dialdehydes such as glyoxal and glutaraldehyde; and derivatives of these aldehydes. The alcohols used in this invention include saturated aliphatic alcohols such as methanol, ethanol, isopropanol and octanol; diols such as ethylene glycol and butanediol; unsaturated aliphatic alcohols such as allyl alcohol; aromatic alcohols such as benzyl alcohol; and phenols.

In the reaction according to this invention, a suitable molar ratio of aldehyde to alcohol is in the range of 10 to 1/1,000, preferably 2 to 1/50. If the molar ratio exceeds 10, decomposition of the aldehyde and other side reactions become noticeable, resulting in a decrease in the selectivity of reaction. Therefore, said ratio is not desirable. On the other hand, if it is less than 1/1,000, the reaction between molecules of alcohol becomes remarkable, also resulting in a decrease in the selectivity of reaction. Thus, this ratio is not desirable.

If necessary, the reaction may be carried out in a solvent having no adverse effect on the progress of the reaction, such as a linear hydrocarbon, for example hexane, nonane or decane. The amount of the solvent may suitably be varied depending upon the reaction conditions.

The oxygen for use in the process of this invention may be molecular oxygen, namely oxygen itself, of a mixed gas containing oxygen gas and a diluent inert to the reaction such as nitrogen or carbon dioxide. Air may also be used. The suitable quantity of oxygen in the reaction system is greater than the stoichiometric quantity required for the reaction and the preferable amount is at least 1.5 times the stoichiometric amount.

As described above, it is essential that the catalyst used in the process of this invention comprises (I) palladium, (II) at least one compound selected from lead compounds, thallium compounds and mercury compounds and (III) at least one compound selected from alkali metal compounds and alkaline earth metal compounds. Only such a combination is able to produce a carboxylic ester in a high yield with a high selectivity, as stated in detail in Examples which appear hereinafter.

Examples of suitable lead compounds include lead oxide, lead hydroxide and lead carboxylates such as lead acetate and lead formate. As the mercury compound, there may be used mercury acetate, mercury nitrate, mercury chloride and mercury oxide. As the thallium compound, there may be used thallium acetate, thallium nitrate, thallium sulfate, thallium chloride and thallium oxide. Examples of suitable compounds of the catalyst component (II) include oxides, hydroxides, carbonates and carboxylic acid salts of the metals. Examples of suitable alkali metal compounds and alkaline earth metal compounds of the catalyst component (III) include oxides, hydroxides, carbonates, sulfates and carboxylates of lithium, sodium, potassium, rubidium, cesium, magnesium, calcium, strontium and barium.

The above catalyst constituents may exist separately in the reaction system though they preferably exist in such forms that they can exert some action to one another. They can be used as supported on a common carrier such as activated carbon, silica or alumina or as supported on one another without using a carrier.

The composition of the catalyst may be varied without particular limitation in a wide range depending upon the types and quantities of the starting materials, method of preparing the catalyst and operational conditions. In general, palladium is in the range of 0.5 to 20%, preferably 1 to 10%, by weight and an alkali metal compound or alkaline earth metal compound is in the range of 0.05 to 95% by weight, based on the weight of the catalyst (including the carrier, if it is used). The atomic ratio of lead, mercury or thallium metal to palladium metal is generally 0.01/1 to 10/1, preferably 0.05/1 to 5.0/1. Although not critical, the amount (in weight) of the catalyst used is 1/1,000 to 20 times the weight of the aldehyde fed. The invention, however, is not limited to such a range, particularly when the reaction is carried out in the flow system.

Preparation of the catalyst is performed in a customary way. For instance, when it is intended to prepare a catalyst by supporting palladium, a lead compound and a magnesium compound on a suitable carrier, an alumina carrier, which has already supported magnesium nitrate and calcined, is impregnated with an aqueous solution of a palladium salt, then reduced with a suitable reducing agent in a customary way, further immersed in, for example, an aqueous solution of lead acetate, and evaporated to dryness to give a supported catalyst ready for use.

The process of this invention is carried out at a temperature in the range of 0° to 200° C., preferably as low as 20° to 120° C. Although the reaction can be conducted under subatmospheric, atmospheric or superatmospheric pressure, one of the features of the process of this invention lies in the simplicity of operation and an intended carboxylic ester can be obtained easily and in a high yield by simply introducing oxygen into the reaction system under atmospheric pressure. The reaction can be carried out either batchwise or continuously.

The process has the following advantages:
(1) The reaction system is a simple one comprising an aldehyde, an alcohol, a molecular oxygen-containing gas and a catalyst; and no complicated reaction procedure is necessary.
(2) Since the catalyst retains a high activity at a temperature as low as about 40° C. and exhibits an excellent selectivity, a carboxylic ester can be easily obtained in one step from an aldehyde and an alcohol.
(3) Since few side reactions take place and the catalyst is a solid mixture, separation and purification of the reaction product are easy and the catalyst remains stable under the reaction conditions.
(4) Because of a high rate of reaction even at low temperatures under atmospheric pressure, the productivity per reactor is very high.

As described in the foregoing, according to this invention, a carboxylic ester is produced in a high yield in one step from an aldehyde and an alcohol. Therefore, the present invention is very valuable from the commercial point of view.

The invention is further illustrated below in detail with reference to Examples which are merely illustrative and not limitative. In the Examples and Comparative Examples, all percentages are by weight unless otherwise indicated.

EXAMPLE 1

In a four-necked flask provided with a gas inlet, a condenser, a stirrer and a thermometer were placed 3.3 g of methacrolein, 100 cc of methanol and 4 g of a catalyst prepared by impregnating a 5%-palladium-calcium carbonate (produced by Engelhard Co.) with an aqueous solution of lead acetate and drying them to support 5.3% of lead acetate on the former. While maintaining the internal temperature of the flask at 40° C., oxygen was passed through the well stirred reactant mixture at a rate of 3.0 liters/hour for 3 hours to allow the reaction to proceed. On analysis of the reaction mixture, it was found that the conversion was 98% and almost all the reaction products were methyl methacrylate (93% yield and 94.8% selectivity). A small amount of methyl formate was found as a by-product. The formation of a dimer and other polymers was hardly observed.

COMPARATIVE EXAMPLE 1

By using a 5%-platinum-calcium carbonate on which 5% of lead acetate was supported as catalyst, the reaction was carried out in the same apparatus, under the same conditions, in the same manner as in Example 1. No formation of methyl methacrylate was observed.

COMPARATIVE EXAMPLE 2

By using as catalyst a 5%-ruthenium-calcium carbonate on which 5% of lead acetate was supported, the reaction was conducted in the same apparatus, under the same conditions, and in the same manner as in Example 1. No formation of methyl methacrylate was noticed.

COMPARATIVE EXAMPLE 3

By using as catalyst a 5%-rhodium-calcium carbonate on which 5% of lead acetate was supported, the reaction was carried out in the same manner as in Example 1. No formation of methyl methacrylate was noticeable.

COMPARATIVE EXAMPLE 4

By using 4 g of the same catalyst as in Example 1, except that no lead acetate was contained, the reaction was conducted under the same conditions as in Example 1. The conversion of methacrolein was 19% and the yield of methyl methacrylate was 10.5% based on methacrolein used as starting material.

EXAMPLE 2

In a four-necked flask provided with a gas inlet, a condenser, a stirrer and a thermometer were placed 3.3 g of methacrolein, 100 cc of methanol and 4 g of a catalyst prepared by supporting on 5%-palladium-calcium carbonate (produced by Engelhard Co.) 1.2% by weight of thallium (I) acetate and then drying. While maintaining the internal temperature of the flask at 40° C., oxygen was introduced through the gas inlet into the well stirred reactant mixture at a rate of 3.0 liters/hour for 3 hours to allow the reaction to proceed. On analysis of the reaction mixture, it was found that the conversion of methacrolein was 97% and almost all the reaction products were methyl methacrylate (91% yield and 94% selectivity). The by-product detected was a small amount of methyl formate and no formation of dimers and other polymers was observed.

EXAMPLE 3

By using 2.6 g of acrolein, 100 cc of ethanol and 4 g of the same catalyst as in Example 2, oxygen was passed through the reactant mixture at 40° C., at a rate of 5 liters/hour, for 2 hours to allow the reaction to proceed. On analysis of the reaction mixture, it was found that the conversion of acrolein was 94%, the yield of ethyl acrylate was 88% and only a small amount of ethyl acetate was detected as by-product.

EXAMPLE 4

The reaction was carried out under the same conditions as in Example 2 by using 3.3 g of methacrolein, 100 cc of ethanol and as catalyst 4 g of a 5%-palladium-calcium carbonate (produced by Engelhard Co.) supporting 1.4% by weight of mercury (II) acetate. After the reaction was effected for 3 hours it was found that the conversion of methacrolein was 98%, the yield of the product, ethyl methacrylate, was 92.5%, and almost all the reaction products were the intended product with some ethyl acetate as by-product.

EXAMPLE 5

In a solution containing 0.88 g of palladium chloride dissolved therein was suspended 10 g of a precipitated calcium carbonate powder. Formalin was added to the well stirred suspension to effect reduction. The suspended powder was collected by filtration, washed with water and dried under reduced pressure. The dried powder was impregnated with an aqueous solution of thallium (I) acetate so as to support 0.6% by weight of thallium (I) acetate after drying. A 5-g portion of the dried catalyst thus prepared, 12.5 g of methacrolein and 100 cc of methanol were placed in the same apparatus as in Example 1 and, while introducing oxygen at a flow rate of 2 liters per hour, they were allowed to react at 50° C. for 5 hours. On analysis of the reaction mixture, it was found that the conversion of methacrolein was 96% and the yield of methyl methacrylate was 87%.

EXAMPLE 6

Into a 200-cc titanium autoclave equipped with a gas inlet and a stirrer were charged 100 cc of methanol, 14 g of methacrolein and 4 g of the same catalyst as in Example 2. The mixture was maintained at a reaction temperature of 60° C. and allowed to react under a total pressure of 20 kg/cm$^2$ and an oxygen partial pressure of 5 kg/cm$^2$ while replenishing the autoclave with oxygen to maintain the partial pressure at this value. Analysis of the reaction mixture at predetermined time intervals showed a methacrolein conversion of 38% and a methyl methacrylate yield of 34% after 2 hours and a methacrolein conversion of 92% and a methyl methacrylate yield of 88% after 6 hours, indicating an increase in the yield with the lapse of time.

EXAMPLE 7

Into the same apparatus as used in Example 1 were charged 10.5 g of methacrolein, 100 cc of methanol and 10 g of a commercial Lindlar catalyst (a palladium-lead acetate-calcium carbonate type produced by Engelhard Co.). Oxygen was introduced into the autoclave at a rate of 5 liters per hour and the reaction was allowed to proceed at 50° C. for 4 hours. After completion of the reaction, the conversion of methacrolein was 97% and the yield of methyl methacrylate, the intended reaction product, was 91%.

EXAMPLES 8 TO 20 AND COMPARATIVE EXAMPLES 5 TO 8

Using the same apparatus as in Example 1, experiments were made with catalysts of various combinations shown in Table 2. The starting materials in each experiment were 3.3 g of methacrolein and 100 cc of methanol. The flow rate of oxygen was 2 liters per hour, the reaction temperature 40° C., and the reaction time 2 hours. In Table 2, "conversion" means the conversion of methacrolein fed, "yield" means the yield of methyl methacrylate based on the methacrolein fed, and "amount obtained" means the weight of the substance in the reaction mixture.

As seen from Table 2, the yield of methyl methacrylate was greatly increased by the addition of the second catalyst component.

and 4 g of a catalyst prepared by supporting on a palladium (5%)-carbon catalyst (product of Engelhard Co.) 0.5% and 20% (in terms of metal) of thallium-(I) acetate and magnesium acetate, respectively. The mixture was allowed to react for 2 hours at a reaction temperature of 40° C. at an oxygen flow rate of 3 liters per hour. After 2 hours of reaction, the methacrolein conversion was 91% and the yield of methyl methacrylate was 72% (79.3% selectivity) based on methacrolein fed.

EXAMPLES 22 TO 28

The reaction procedure of Example 21 was repeated, except that the catalyst used were as shown in Table 3, in which the results obtained were also shown. In Table 3, the catalyst composition was expressed in terms of metal content in the catalyst; "conversion" means the conversion of methacrolein fed; "yield" means the yield Table 2

| Example No. | First catalyst component | (g) | second catalyst component | (mg) | Methacrolein conversion (%) | Methyl methacrylate yield (%) | Amount of methyl methacrylate obtained (g) |
| --- | --- | --- | --- | --- | --- | --- | --- |
| 8 | Pd(5%)/CaCO$_3$ | 4 | Lead nitrate | 63 | 77 | 61 | 2.88 |
| 9 | " | 4 | Lead stearate | 146 | 82 | 56 | 2.65 |
| 10 | " | 6 | Lead oxide | 320 | 87 | 68 | 3.20 |
| 11 | " | 4 | Thallium (I) nitrate | 40 | 82 | 76 | 3.58 |
| 12 | " | 4 | Thallium (I) chloride | 45 | 83 | 65 | 3.07 |
| 13 | " | 4 | Thallium (I) acetate | 50 | 90 | 78 | 3.68 |
| 14 | " | 6 | Thallium (I) carbonate | 45 | 88 | 74 | 3.50 |
| 15 | Pd(5%)/MgO | 4 | Lead acetate | 71 | 92 | 54 | 2.55 |
| 16 | " | 4 | Lead acetate + sodium acetate | 71 + 200 | 92 | 63 | 2.95 |
| 17 | " | 4 | Mercury (II) acetate | 60 | 96 | 68 | 3.20 |
| 18 | " | 4 | Thallium (II) oxide | 43 | 84 | 66 | 3.10 |
| 19 | " | 6 | Thallium (I) nitrate | 55 | 100 | 82 | 3.85 |
| 20 | Pd(5%)/activated carbon | 6 | Thallium (I) acetate + potassium acetate | 50 + 200 | 96 | 78 | 3.68 |
| Comparative Example 5 | Pd(5%)/CaCO$_3$ | 4 | — | — | 15 | 7 | 0.33 |
| Comparative Example 6 | Pd(5%)/MgO | 4 | — | — | 93 | 35 | 1.65 |
| Comparative Example 7 | Pd(5%)/alumina | 4 | — | — | 97 | 31 | 1.45 |
| Comparative Example 8 | Pd(5%)/activated carbon | 4 | — | — | 92 | 40 | 1.90 |

EXAMPLE 21

In a four-necked flask provided with a gas inlet, a stirrer, a reflux condenser and a thermometer at the top were placed 3.3 g of methacrolein, 100 cc of methanol of methyl methacrylate based on methacrolein fed, and "selectivity" means the percentage of the amount of methyl methacrylate formed based on the amount of methacrolein reacted.

Table 3

| Example No. | Catalyst Type | Composition (% in terms of metal) | Amount used (g) | Conversion (%) | Yield (%) | Selectivity (%) |
| --- | --- | --- | --- | --- | --- | --- |
| 22 | Pd-mercury acetate-MgO-silica | Pd—Hg—Mg (5) (0.5) (30) | 4 | 77 | 60 | 78.0 |
| 23 | Pd-thallium acetate-SrO-silica | Pd—Tl—Sr (5) (0.4) (10) | 4 | 70 | 59 | 84.3 |
| 24 | Pd-lead acetate-BaO-silica | Pd—Pb—Ba (5) (2) (10) | 4 | 66 | 61 | 92.5 |
| 25 | Pd-lead acetate-barium carbonate | Pd—Pb—Ba (5) (2) (64) | 6 | 43 | 38 | 88.2 |
| 26 | Pd-lead acetate-BaSO$_4$ | Pd—Pb—Ba | 6 | 46 | 43 | 93.5 |

Table 3-continued

| Example No. | Catalyst Type | Composition (% in terms of metal) | Amount used (g) | Conversion (%) | Yield (%) | Selectivity (%) |
|---|---|---|---|---|---|---|
| 27 | Pd-mercury acetate-SrCO₃ | (5) (3) (54) Pd—Hg—Sr | 6 | 58 | 50 | 86.4 |
| 28 | Pd-Tl₂O₃—MgCO₃ | (5) (0.5) (56) Pd—Tl—Mg (5) (0.5) (27) | 14 | 88 | 75 | 85.1 |

EXAMPLE 29

In an aqueous solution containing 0.88 g of palladium chloride dissolved therein was immersed 10 g of silica gel supporting 10% of lithium carbonate. After evaporation to dryness, the resulting solid was reduced with formalin and then treated so as to support 5% by weight of lead acetate thereon. Ten grams of the resulting catalyst was filled in a tubular reactor, 10 mm in diameter. From the upper end of the reactor maintained at 60° C. were fed 25 cc/hour of a methanol solution containing 8% by weight of methacrolein and 2 liters/hour of air to carry out the reaction in a continuous flow system. The conversion of methacrolein, the yield of methyl methacrylate based on methacrolein fed, and the selectivity were 71%, 64% and 90.2%, respectively, after two hours of reaction and 74%, 63% and 89.6%, respectively, after 200 hours of reaction, indicating that the reaction proceeded in a substantially steady state.

EXAMPLES 30 TO 33

Using the same apparatus as in Example 29 and in a similar manner to Example 29, several catalysts having varying compositions were tested. The results obtained were as shown in Table 4. The catalysts were prepared similarly to Example 29. The alkali metal compounds used as starting materials were carbonates in Examples 30 and 31 and acetates in Examples 32 and 33. The lead compounds were added all in the form of acetate. In each case 10 g of the carrier was used.

| Example 30 | Sodium carbonate | 460 mg |
|---|---|---|
|  | Lead acetate | 915 mg |
| Example 31 | Potassium carbonate | 530 mg |
|  | Lead acetate | 915 mg |
| Example 32 | Rubidium acetate | 338 mg |
|  | Lead acetate | 915 mg |
| Example 33 | Cesium acetate | 144 mg |
|  | Lead acetate | 915 mg |

EXAMPLE 34

In an aqueous solution containing 17.9 g of magnesium acetate [Mg(OAc)₂.4H₂O] and 9.15 g of lead acetate [Pb(OAc)₂.3H₂O] dissolved therein was immersed 100 g of granular alumina. The mixture was evaporated with thorough stirring to dryness, dried thoroughly, and calcined in a furnace at 800° C. for 3 hours. The calcined product was immersed in an aqueous solution containing 4.18 g of palladium chloride and acidified with hydrochloric acid, dried, then subjected to reduction with formalin, thereafter washed with water, and dried to obtain a catalyst. Ten grams of the catalyst was weighed out and filled in the same reactor as in Example 29. From the upper end of the reactor were fed 25 cc/hour of a methanol solution containing 7.0% by weight (based on methanol) of methacrolein and $4.2 \times 10^{-2}$% by weight of magnesium acetate, and 2 liters/hour of air. The liquid accumulated in a trap below the reactor was analyzed at predetermined time intervals to examine the progress of the reaction. The conversion of methacrolein and the yield of methyl methacrylate were 84.5% and 73.5%, respectively, at the 100th hour of reaction and 84.5% and 74.4%, respectively, at the 1000th hour of reaction, indicating that the catalyst still retained the catalytic activity.

EXAMPLE 35

In the same apparatus as in Example 1 were placed 10 g of isobutyraldehyde, 100 cc of methanol, and a catalyst prepared by supporting 5% of palladium on 10 g of magnesium oxide-supported alumina by an impregnation method, and supporting thereon 0.6% of thallium (I) acetate by an impregnation method. While feeding 2 liters/hour of oxygen, the mixture was allowed to react at 45° C. for 2 hours. On analysis of the reaction mixture, it was found that the conversion of isobutyraldehyde was 42% and the yield of methyl isobutyrate was 38% based on isobutyraldehyde fed, indicating excellent selectivity.

EXAMPLES 36 TO 46

Tests were conducted on various combinations of aldehydes and alcohols by using the same apparatus as in Example 1 and the same commercial Lindlar catalyst as in Example 7. The results obtained were as shown in Table 4

| Example No. | Catalyst composition (% in terms of metal) | Reaction conditions | | | | | Results in 2nd hour | | Results in 200th hour | |
|---|---|---|---|---|---|---|---|---|---|---|
| | | MAcr/MeOH (wt-%) | Feed rate (cc/hr) | Air (liter/hour) | Temp. (°C.) | Amount of catalyst (g) | MAcr conv. (%) | MMA yield (%) | MAcr conv. (%) | MMA yield (%) |
| 30 | Pd—Pb—Na-alumina (2) | 7.0 | 25 | 2.0 | 50 | 10 | 83 | 75 | 81 | 74 |
| 31 | Pd—Pb—K-alumina (1) | " | " | " | 60 | " | 70 | 65 | 67 | 64 |
| 32 | Pd—Pb—Rb-silica (2.5) | " | " | " | " | " | 77 | 70 | 71 | 67 |
| 33 | Pd—Pb—Cs-silica (2) | 20.0 | 30 | 4.0 | " | 20 | 64 | 52 | 58 | 49 |

Table 5. In the table, "yield" is the molar yield of an ester based on the aldehyde fed and "selectivity" is the percentage of the amount of product based on the amount of aldehyde reacted.

the weight of the catalyst (including carrier if one is used), the amount of alkali metal compound or alkaline earth metal compound is 0.05 to 95% by weight based on the weight of the catalyst (including carrier if one is used), and the atomic ratio of lead, mercury or thallium metal to palladium metal is 0.01/1 to 10/1.

Table 5

| Example No. | Reaction conditions | | | | | | | | Result | | |
|---|---|---|---|---|---|---|---|---|---|---|---|
| | Aldehyde | (cc) | Alcohol | (cc) | Catalyst (g) | Air (liter/hour) | Temp. (°C.) | Reaction time (hour) | Main product | Yield (%) | Selectivity (%) |
| 36 | 2-Ethylhexylaldehyde | (5) | Methanol | (100) | 5 | 2.0 | 100 | 2 | Methyl 2-ethylhexoate | 78 | 90 |
| 37 | Benzaldehyde | (8) | Ethanol | (100) | 5 | 2.5 | 60 | 2 | Ethyl benzoate | 65 | 92 |
| 38 | Propionaldehyde | (10) | n-Octanol | (100) | 5 | 3.0 | 50 | 2 | n-Octyl propionate | 58 | 91 |
| 39 | Acetaldehyde | (10) | n-Butyl alcohol | (100) | 5 | 3.0 | 40 | 2 | n-Butyl acetate | 87 | 92 |
| 40 | " | (20) | Isobutyl alcohol | (100) | 5 | 3.0 | 40 | 2 | Isobutyl acetate | 41 | 91 |
| 41 | " | (20) | Isopropanol | (50) | 10 | 3.0 | 40 | 2 | Isopropyl acetate | 33 | 94 |
| 42 | Isobutyraldehyde | (10) | Benzyl alcohol | (50) | 5 | 2.0 | 60 | 4 | Benzyl isobutyrate | 67 | 92 |
| 43 | Crotonaldehyde | (5) | Ethanol | (100) | 5 | 3.0 | 70 | 3 | Ethyl crotonate | 86 | 91 |
| 44 | Acetaldehyde | (10) | Methanol + n-hexane | (50) (50) | 5 | 5.0 | 40 | 2 | Methyl acetate | 93 | 95 |
| 45 | Methacrolein | (15) | Methanol + n-decane | (50) (50) | 10 | 3.0 | 60 | 3 | Methyl methacrylate | 88 | 90 |
| 46 | Glutaraldehyde | (5) | Methanol | (100) | 5 | 5.0 | 50 | 2 | Dimethyl glutarate | 84 | 86 |

What is claimed is:

1. In a process for producing a carboxylic ester by the reaction between an aldehyde and an alcohol in the presence of oxygen with a catalyst at a temperature of 0° to 200° C., the improvement wherein the catalyst consists essentially of (I) palladium, (II) at least one compound selected from the group consisting of lead compounds, thallium compounds and mercury compounds and (III) at least one compound selected from the group consisting of alkali metal and alkaline earth metal oxides, hydroxides, carbonates and carboxylic acid salts.

2. A process according to claim 1, wherein the aldehyde is acrolein or methacrolein and the alcohol is methanol or ethanol.

3. A process according to claim 1, wherein the lead compounds, thallium compounds and mercury compounds are oxides, hydroxides, carbonates or carboxylic acid salts of said metals.

4. A process according to claim 1, wherein the amount of palladium is 0.5 to 20% by weight based on the weight of the catalyst (including carrier if one is used).

5. A process according to claim 1, wherein the amount of catalyst is one thousandth to 20 times the weight of aldehyde.

6. A process according to claim 1, wherein the catalyst is supported on silica or alumina.

7. A process according to claim 1, wherein the molar ratio of the aldehyde to the alcohol is from 10 to 1/1,000.

8. A process according to claim 1, wherein the aldehyde is a member selected from the group consisting of saturated aliphatic aldehydes, unsaturated aliphatic aldehydes and aromatic aldehydes, and the alcohol is a member selected from the group consisting of saturated aliphatic alcohols, unsaturated aliphatic alcohols and aromatic alcohols.

9. A process according to claim 1, wherein (III) is at least one alkaline earth metal oxide, hydroxide, carbonate or carboxylic acid salt.

* * * * *